US010736764B2

(12) United States Patent
Dean et al.

(10) Patent No.: US 10,736,764 B2
(45) Date of Patent: Aug. 11, 2020

(54) DUODENAL SLEEVE AND ANCHOR AND METHODS OF IMPLANTATION

(71) Applicant: Apollo Endosurgery US, Inc., Austin, TX (US)

(72) Inventors: Charles Dean, Austin, TX (US); Donald K. Jones, Dripping Springs, TX (US)

(73) Assignee: Apollo Endosurgery US, Inc., Austin, TX (US)

(*) Notice: Subject to any disclaimer, the term of this patent is extended or adjusted under 35 U.S.C. 154(b) by 694 days.

(21) Appl. No.: 15/419,200

(22) Filed: Jan. 30, 2017

(65) Prior Publication Data

US 2018/0214293 A1 Aug. 2, 2018

(51) Int. Cl.
*A61F 5/00* (2006.01)

(52) U.S. Cl.
CPC .......... *A61F 5/0089* (2013.01); *A61F 5/0033* (2013.01); *A61F 5/0076* (2013.01); *A61F 5/0079* (2013.01)

(58) Field of Classification Search
CPC .... A61F 5/0089; A61F 5/0033; A61F 5/0076; A61F 5/0079
See application file for complete search history.

(56) References Cited

U.S. PATENT DOCUMENTS

| | | | |
|---|---|---|---|
| 7,037,344 B2 | 5/2006 | Kagan et al. | |
| 7,682,330 B2 | 3/2010 | Meade et al. | |
| 7,695,446 B2 | 4/2010 | Levine et al. | |
| 7,766,861 B2 | 8/2010 | Levine et al. | |
| 7,803,195 B2 | 9/2010 | Levy et al. | |
| 7,815,591 B2 | 10/2010 | Levine et al. | |
| 7,976,488 B2 | 7/2011 | Levine et al. | |
| 7,981,163 B2 | 7/2011 | Meade et al. | |
| 8,057,420 B2 | 11/2011 | Meade et al. | |
| 8,142,385 B2 | 3/2012 | Grau et al. | |
| 8,177,853 B2 | 5/2012 | Stack et al. | |
| 8,182,442 B2 | 5/2012 | Grau et al. | |
| 8,211,186 B2 | 7/2012 | Belhe et al. | |
| 8,221,505 B2 | 7/2012 | Skerven | |
| 8,308,813 B2 | 11/2012 | Krueger et al. | |
| 8,491,519 B2 | 7/2013 | Chin | |
| 8,574,184 B2 | 11/2013 | Errico et al. | |
| 8,579,849 B2 | 11/2013 | Grau et al. | |
| 8,628,583 B2 | 1/2014 | Meade et al. | |
| 8,771,219 B2 | 7/2014 | Meade et al. | |

(Continued)

OTHER PUBLICATIONS

Endobarrier® Procedure, GI Dynamics, Inc., 2014 (2 pages).

(Continued)

*Primary Examiner* — Philip R Wiest
(74) *Attorney, Agent, or Firm* — Donald K. Jones

(57) ABSTRACT

A gastric implant includes a distal sleeve portion configured to be disposed in a duodenum of a patient, and a pyloric restriction portion connected to a proximal end of the distal sleeve portion. The pyloric restriction portion is configured to be disposed in a pylorus of a patient. Also, the implant includes a proximal anchor portion connected to a proximal end of the pyloric restriction portion. The proximal anchor portion is configured to be disposed in a lower stomach of the patient. The proximal anchor portion has at least one eyelet for fastening to the stomach to secure the implant to the gastrointestinal tract.

9 Claims, 10 Drawing Sheets

(56) References Cited

U.S. PATENT DOCUMENTS

| | | |
|---|---|---|
| 8,784,500 B2 | 7/2014 | Stack et al. |
| 8,870,808 B2 | 10/2014 | Grau et al. |
| 8,882,698 B2 | 11/2014 | Levine et al. |
| 8,911,393 B2 | 12/2014 | Levy et al. |
| 9,155,650 B2 | 10/2015 | Birk |
| 2003/0040804 A1 | 2/2003 | Stack et al. |
| 2004/0117031 A1* | 6/2004 | Stack .................... A61F 2/04 623/23.65 |
| 2008/0065136 A1 | 3/2008 | Young |
| 2008/0208357 A1 | 8/2008 | Melanson et al. |
| 2009/0012541 A1 | 1/2009 | Dahl et al. |
| 2009/0299486 A1 | 12/2009 | Shohat et al. |
| 2010/0256775 A1 | 10/2010 | Belhe et al. |
| 2012/0065571 A1* | 3/2012 | Thompson ............ A61F 5/0076 604/8 |
| 2012/0172999 A1 | 7/2012 | Binmoeller |
| 2014/0350694 A1 | 11/2014 | Behan |
| 2016/0000549 A1 | 1/2016 | Gittard et al. |

OTHER PUBLICATIONS

The EndoBarrier® Gastrointestinal Liner with Delivery System, Instructions for Use, 50-10-00552 Rev N, GI Dynamics, Inc., (9 pages).

* cited by examiner

DUODENAL SLEEVE AND ANCHOR AND METHODS OF IMPLANTATION

BACKGROUND

1. Field

The present disclosure relates to an implantable duodenal sleeve and stomach anchor, a delivery system, and methods of implanting the sleeve.

2. State of the Art

A duodenal-jejunal bypass sleeve (DJBS), such as the EndoBarrier Gastrointestinal Liner available from GI Dynamics Inc., Lexington, Mass., USA, is an endoscopically and fluoroscopically inserted implant. The EndoBarrier is an impermeable fluoropolymer sleeve that is reversibly fixated to the duodenal bulb and extends 80 cm into the small bowel, usually terminating in the proximal jejunum. It allows transit of chyme from the stomach through to the jejunum without contact with the duodenal wall. By not allowing mixing with pancreatic exocrine secretions and bile in the jejunum, it mimics a duodenal-jejunal bypass and encourages weight loss through malabsorption. The Endobarrier is contained within a capsule and is inserted in the duodenum endoscopically. The sleeve is then deployed distally into the proximal jejunum under fluoroscopic control. This procedure helps patients regain metabolic control of Type II diabetes and aid in weight loss.

SUMMARY

According to one aspect of the disclosure, further details of which are provided below, a gastric implant includes a distal sleeve portion, a pyloric restriction portion, and a proximal anchor portion. The distal sleeve portion, the pyloric restriction portion, and the proximal anchor portion may define a common passageway for conducting contents of the stomach from the stomach through the passageway to the duodenum.

The distal sleeve portion is configured to be disposed in a duodenum of a patient. The distal sleeve portion includes a wall that is at least partly formed of a film, which may be made from at least one of polyethylene terephthalate (PET), polytetrafluoroethylene (PTFE), expanded polytetrafluoroethylene (ePTFE), polyester, and polyethylene. The distal sleeve is configured to be radially expandable from a compressed delivery configuration to an implanted configuration. The film of the wall may have an expandable characteristic. Additionally or alternatively, the sleeve may include an expandable framework within or outside and coupled to the film wall to provide such an expandable characteristic. For example, the film wall may be molded over an expandable metal coil or mesh, and shape memory alloy.

The pyloric restriction portion is connected to a proximal end of the distal sleeve portion and is configured to be disposed in the pylorus of a patient. The gastric implant may optionally also include a sealing portion around the pyloric restriction portion. The sealing portion may be configured to seal against the pylorus of the patient or at least partially fill space between the pyloric restriction portion and the pylorus. The sealing portion may include at least one of an inflatable balloon, an expandable hydrogel, and an expandable member.

The proximal anchor portion is connected to a proximal end of the pyloric restriction portion and is configured to be disposed in a lower stomach of the patient. The proximal anchor portion has at least one eyelet for fastening to the stomach to secure the implant to the gastrointestinal tract. The proximal anchor portion may include at least one of an expandable framework and a film. The expandable framework may include at least one of an expandable metal coil, mesh, shape memory alloy, and a polymeric film. The film may include at least one of PET, PTFE, ePTFE, polyester, and polyethylene.

According to yet another aspect of the disclosure, further details of which are provided below, a gastric implant and delivery assembly includes a gastric implant configurable from an elongate delivery configuration to an implanted configuration. The gastric implant has eyelets for fastening to a gastrointestinal tract of a patient. The implant may be configured to be radially expandable when the implant is reconfigured from the elongate delivery configuration to the implanted configuration. Additionally or alternatively, in the delivery configuration the implant may be constrained in a radially reduced configuration and released from the constraint in the implanted configuration.

The assembly also includes a delivery system configured to receive and deliver the gastric implant at a target location in the gastrointestinal tract of the patient. The delivery system includes an outer sheath, an intermediate sheath that is radially spaced inward of the outer sheath, an inner sheath disposed radially inward of the intermediate sheath, and a cap connected to a distal end of the inner sheath. The outer sheath, intermediate sheath, and the inner sheath are configured for relative axial displacement relative to one another. The gastric implant is disposed in the elongate delivery configuration between the outer sheath and the intermediate sheath, and proximal of the cap. The delivery system is configured to deploy the implant from the delivery configuration to the implanted configuration by retracting the outer sheath relative to the intermediate sheath to expose an outer surface of the implant.

In the delivery configuration, a distal end of the implant may be retained between the cap and the intermediate sheath. The delivery system is configured to release the distal end of the implant from the delivery system by withdrawing the intermediate sheath relative to the inner sheath, and optionally displacing the cap relative to the distal end of the implant, permitting the distal end of the implant to expand relative to the radially constrained delivery configuration.

According to another aspect of the disclosure, further details of which are provided below, a method of delivering and implanting a gastric implant in the gastrointestinal tract of a patient includes providing the implant in a delivery catheter, and delivering the gastric implant to a target location of the gastrointestinal tract. The target location may include at least one of the stomach, duodenum, and the pylorus. The implant may be delivered endoscopically.

Also, the method includes deploying the implant with the delivery catheter at the target location, and fastening an anchor portion of the implant to the lower stomach of the gastrointestinal tract. The implant may be fastened with at least one suture or deployable fastener. In one embodiment, the implant may have at least one eyelet that may be sutured or otherwise fastened to the stomach.

According to another aspect of the disclosure, further details of which are provided below, a method of placing an implantable sleeve with eyelets in a gastrointestinal tract of a patient includes providing a delivery system containing the sleeve, introducing a guidewire into the gastrointestinal tract of a patient, and advancing the delivery system along the guidewire to a target location in the gastrointestinal tract at which to place the implantable sleeve. The target location may include at least one of the duodenum, the pylorus, and the stomach.

Also, the method includes deploying the implantable sleeve from the delivery system to permit expansion of the sleeve to a diameter larger than a diameter of the delivery system, and withdrawing at least a portion of the delivery system from the gastrointestinal tract of the patient through a lumen defined through the expanded sleeve. The method may further include fastening the eyelets of the deployed sleeve to the gastrointestinal tract.

DETAILED DESCRIPTION

Figure 1:
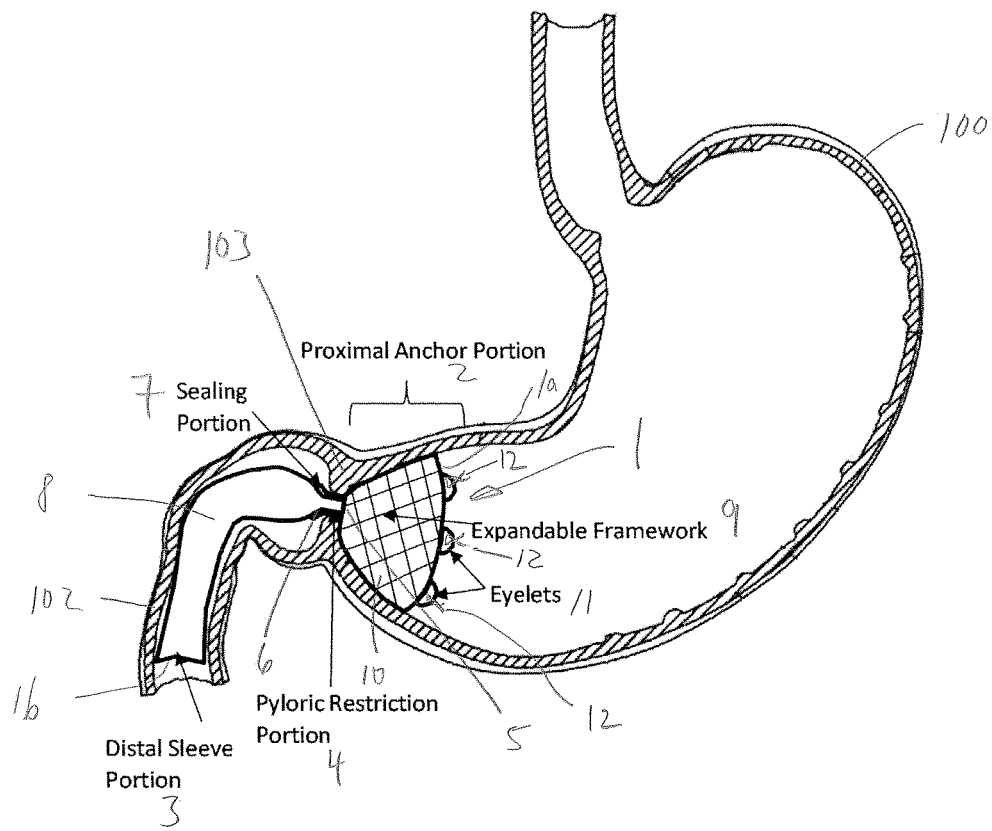
FIG. 1 is a section view of a gastric implant device in an implanted configuration in a stomach of a patient.

FIG. 1 is a view of a gastric implant 1 shown implanted in a stomach 100 of a patient. The implant 1 includes a proximal anchor portion 2, a distal sleeve portion 3, and a pyloric restriction portion 4. The implant extends from a proximal end 1a at the proximal anchor portion 2 to a distal end 1b at the distal sleeve portion 4. A continuous passageway 8 is defined through the implant 1 from the proximal end 1a to the distal end 1b. The implant 1 is configured to route stomach contents (e.g., chyme) from the stomach 100 to the duodenum 102 through the passageway 8.

The proximal anchor portion 2 is configured to be located in a lower portion of the stomach 100, near the pylorus 103. The proximal anchor portion 2 is formed of at least one of an expandable framework 9 and a film 10 that is configured to conform closely to the contour of the stomach 100 near the pylorus 103. The framework 9 may be formed from an expandable coil, wire mesh, a shape memory alloy (e.g., nitinol), or polymeric film. The film 10 may be formed from a biocompatible plastic material that can remain undamaged in the stomach for at least six months. Examples of materials of the film include polyethylene terephthalate (PET), polytetrafluoroethylene (PTFE), expanded polytetrafluoroethylene (ePTFE), polyester, and polyethylene. It is preferred that the outer side of the proximal anchor portion 2 contact and seal to the inner stomach wall to minimize fluid from bypassing the passageway of the implant 1. However, even if some fluid from the stomach bypasses the implant 1, most fluid will not be bypassed and the implant will remain effective in reducing nutrient absorption and, therefore, weight loss.

The proximal anchor portion 2 is configured to be folded into a generally linear delivery configuration to fit within a delivery system, described in greater detail below, which can be passed transorally through the esophagus, into the stomach, and into the duodenum. The framework 9 and/or film 10 preferably are biased to automatically expand radially outwardly to the implanted configuration shown in FIG. 1 when released or otherwise deployed from the linear delivery configuration.

The proximal anchor portion 2 has eyelets 11 or anchors that may be used with later deployed fasteners (e.g., sutures 12, FIG. 13) to secure the proximal anchor portion 2 to the interior wall of the stomach 100. The eyelets 11 may be located at the proximal end 1a of the implant 1, as shown in FIG. 1. Preferably, endoscopic surgical techniques may be used to fasten or otherwise secure (e.g., suture) the eyelets 11 to the stomach 100. While it is possible to secure the anchor portion to the stomach wall by using the wire mesh or framework, the wire mesh or framework typically may not have a structural integrity equivalent to that of the eyelets, which may lead to the breaking of struts or damage to the film and sub-optimal performance or complications. One preferred endoscopic suture technique is to use the OverStitch™ Endoscopic Suturing System available from Apollo Endosurgery, Inc., to suture the eyelets to the stomach.

The distal sleeve portion 3 is configured to be located in the duodenum 102. A wall of the distal sleeve portion 3 is formed from a film, which may include at least one of PET, ePTFE, polyester, and polyethylene. The wall of the distal sleeve portion 3 may be impermeable or partially permeable to fully or partially block nutrient absorption in the portion of the intestine in which the distal sleeve portion 3 resides. Thus, the implant may facilitate weight loss in the patient by reducing or eliminating nutrient absorption in a portion of the gastrointestinal tract.

The distal sleeve portion 3 is configured to be radially expandable from a compressed delivery configuration to an implanted configuration. The distal sleeve portion 3 may have a film wall thickness of 0.0007 inch to 0.0015 inch and may have an expanded diameter (when unrestrained outside of the duodenum) of about 15 mm. The film of the wall may have an expandable characteristic. Additionally or alternatively, the distal sleeve portion 3 may include an expandable framework within or without the film wall to provide such an expandable characteristic. For example, the film wall may be molded over or otherwise provided with an expandable metal coil, mesh, or shape memory alloy (e.g., nitinol).

The pyloric restriction portion 4 extends between a distal end 5 of the proximal anchor portion 2 and a proximal end 6 of the distal sleeve portion 3. The pyloric restriction portion 4 is configured to be located in the pylorus 103. The pyloric restriction portion 4 has a wall that may be continuous with the wall of the distal sleeve portion 3. Also, the wall of the pyloric restriction portion 4 may be formed of the same materials as those of the distal sleeve portion 4, and may be integrally formed therewith. Thus, the pyloric restriction portion 4 may have a wall that includes a film formed of at least one of PET, PTFE, ePTFE, polyester and polyethylene. Also, as with the distal sleeve portion 3, the pyloric restriction portion 4 may incorporate a wound coil, wire mesh, or an expandable stent-like structure. The pyloric restriction portion 4 is biased to expand radially outwardly via memory characteristics of the materials of its wall. More specifically, the pyloric restriction portion is configured to be compressed into a linear delivery configuration and expanded when placed in the pylorus in the implanted configuration shown in FIG. 1.

Optionally, the implant may include a sealing portion 7, which may be included around (partially or completely) the pyloric restriction portion 4 at the junction between the pyloric restriction portion 4 and the distal sleeve portion 3. The sealing portion 7 is configured to be positioned within the duodenal bulb and the pylorus 103. The sealing portion 7 may be configured to expand and fill space between the pyloric restriction portion 4 and the pylorus 103 to partially or fully seal between the pyloric restriction portion 3 and the pylorus 103. In a case where the sealing portion 7 only partially seals between the pyloric restriction portion 3 and the pylorus, some amount of chyme in the stomach may bypass the implant 1 and flow from the stomach to the duodenum through a gap between the sealing portion 7 and the pylorus 103. However, even in such a case, it is expected that most chyme will pass through the implant 1 so that nutrient absorption will still be reduced in comparison to a case where the implant 1 is not implanted in the patient.

The sealing portion 7 may take the form of an inflatable balloon (not shown) that can be inflated to expand radially outwardly to become closer to and/or seal with the duodenal bulb and the pylorus 103. Also, the sealing portion 7 may be an expandable hydrogel that can expand closer to and/or seal with the duodenal bulb and the pylorus 103 when the hydrogel is exposed to water in the physiological environment of the duodenal bulb and the pylorus 103. More generally, the sealing portion 7 may take the form of various other expandable members that can expand towards and/or against the duodenal bulb and the pylorus 103. By way of example, and not limitation, such other expandable members may include pleated or umbrella-like or petalloid-like expandable structures that may expand radially outwardly from the outer surface of the pyloric restriction portion 4.

Figure 2:
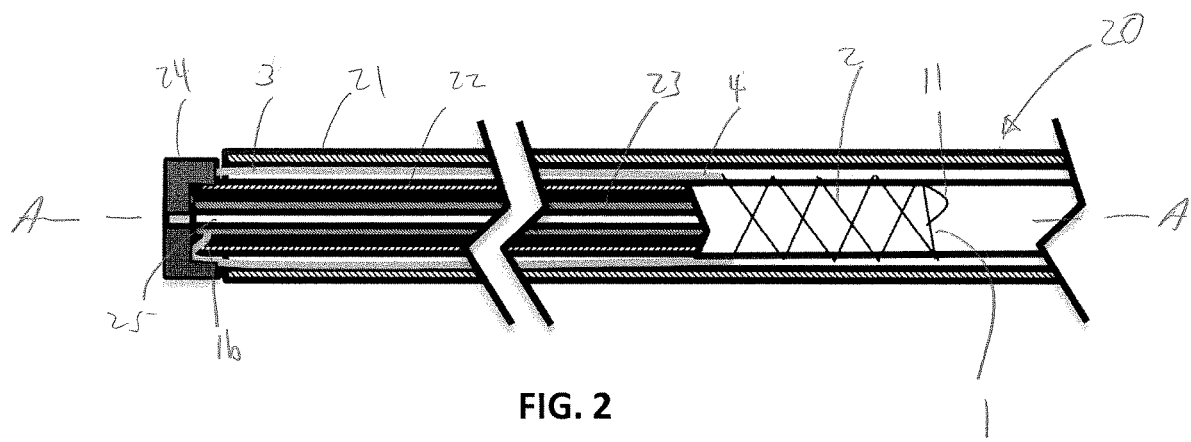
FIG. 2 is a section view of the gastric implant of FIG. 1 folded into a delivery configuration within a sleeve delivery system.
Figure 3:
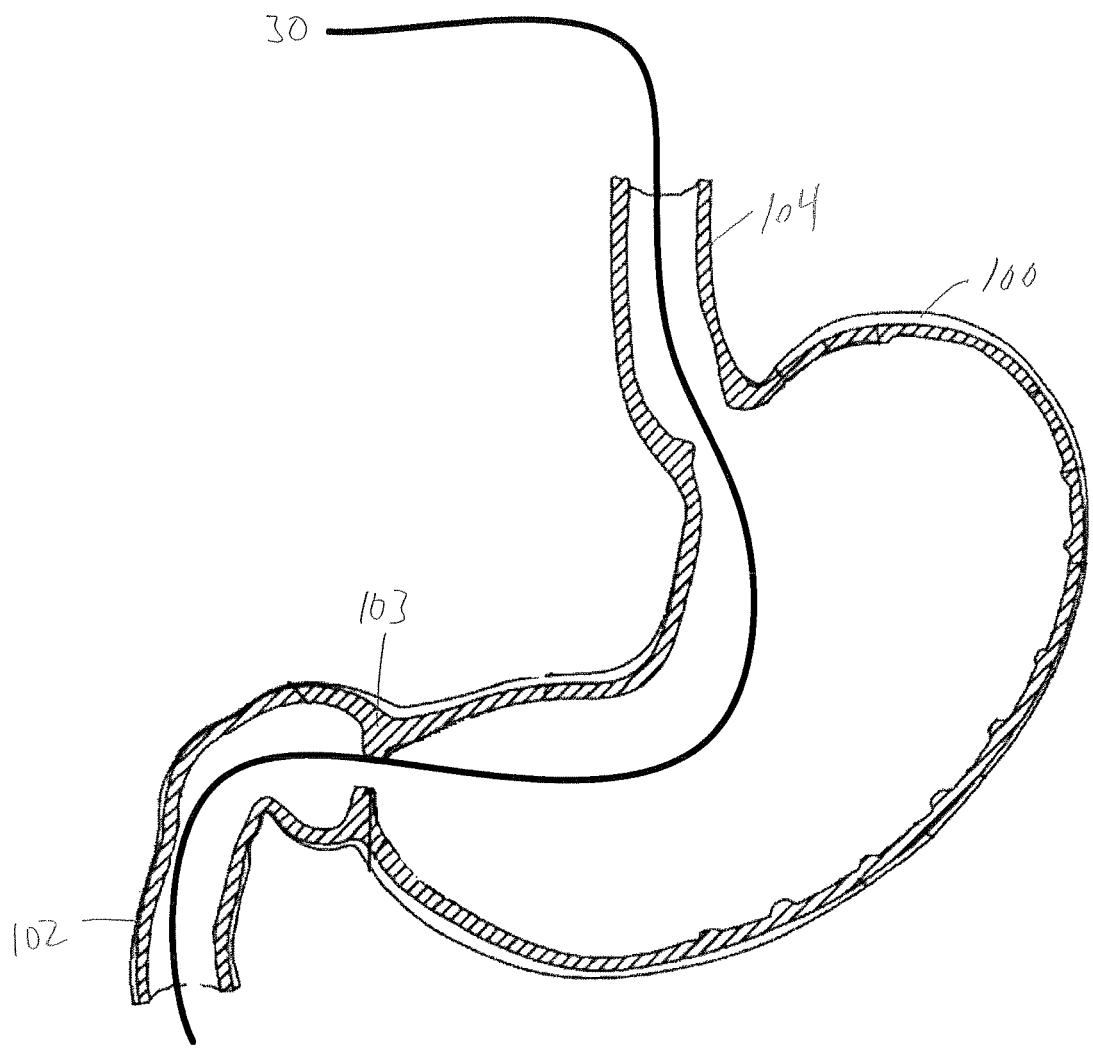
FIG. 3 is a section view of the stomach of FIG. 1 shown with a guidewire inserted into the duodenum.

The implant 1 may be folded into a linear delivery configuration within a delivery sleeve system 20, as shown in FIG. 2. The outer diameter of the delivery system is about 3 millimeters. The delivery sleeve system 20 includes an elongated outer sheath 21 or catheter, an intermediate sheath 22 or catheter, an inner sheath 23 or catheter, and a cap 24. The inner sheath 23 and cap 24 define a passageway 25, coaxial with the passageway 8 of the implant 1, through which a guidewire may also pass during implantation of the implant 1, as will be described in greater detail below.

The distal sleeve portion 3 and the pyloric restriction portion 4 are sandwiched between the outer sheath 21 and the intermediate sheath 22. Located radially adjacent and inward of the intermediate sheath 22 is the inner sheath 23, which is configured to slide or translate axially with respect to the intermediate sheath 22. A distal end of the inner sheath 23 is connected to the cap 24. A distal end 1b of the distal sleeve portion 3 is folded and captured between the cap 24, the intermediate sheath 22, and the inner sheath 23. As will be described below, retracting the intermediate sheath 22 relative to the inner sheath 23 can release the captured distal end 1b of the distal sleeve portion 3 to allow the distal sleeve portion 3 to expand into its implanted configuration.

Figure 4:
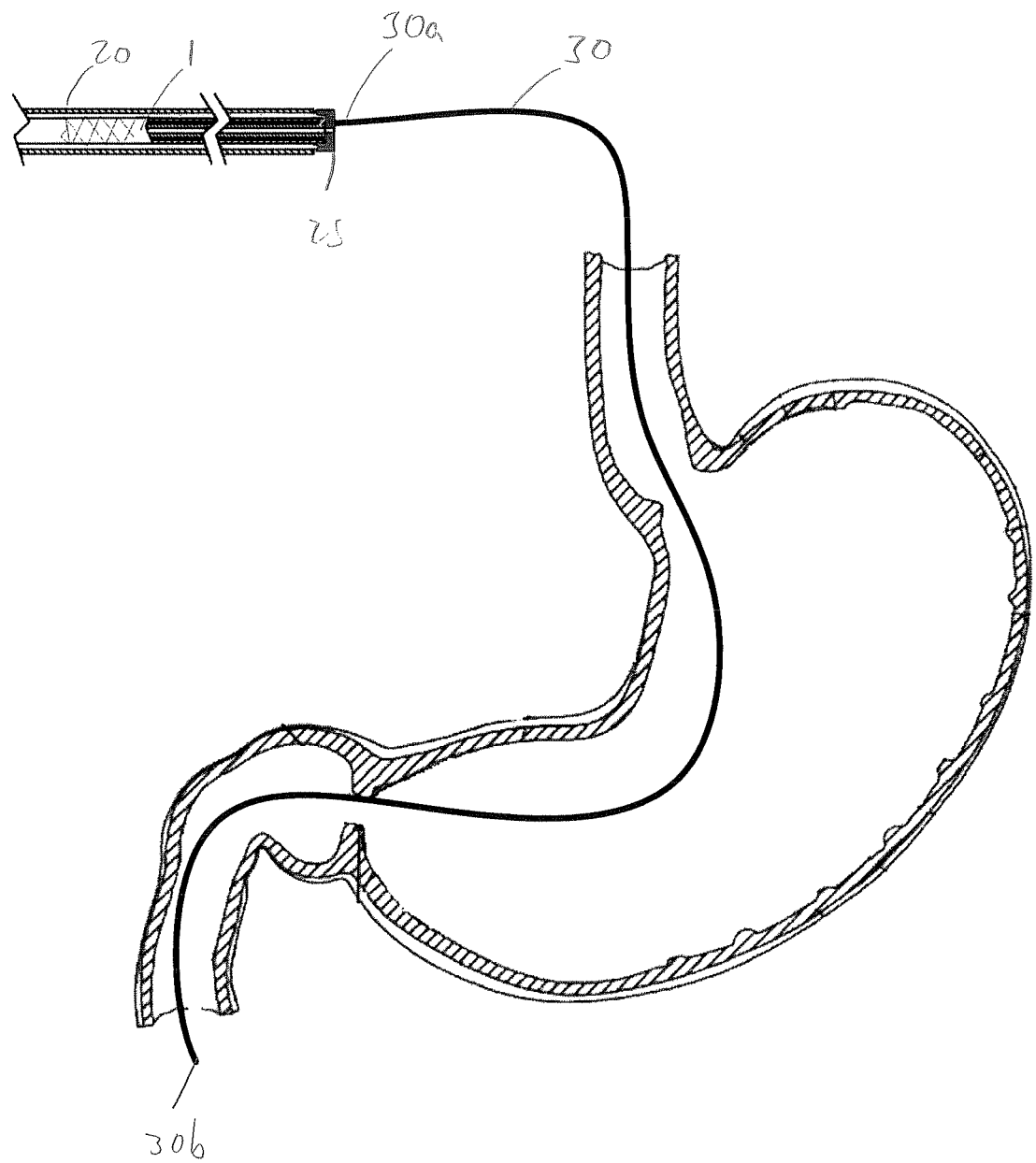
FIG. 4 shows the coupling of the gastric implant and delivery system coupled to the guidewire of FIG. 3 outside of the body of the patient.
Figure 5:
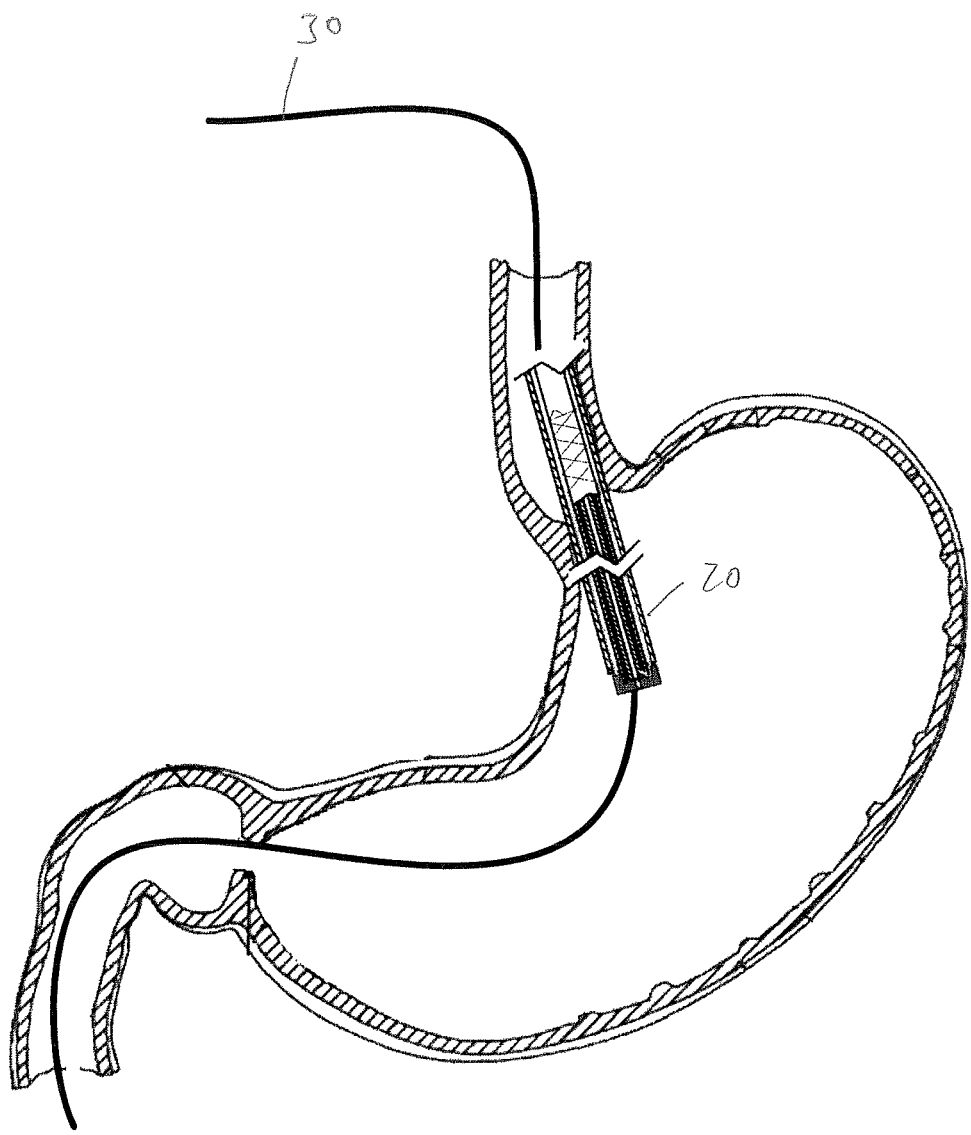
FIG. 5 shows the delivery system and the gastric implant advanced along the guidewire at the GE junction.

A procedure for implanting the implant device 1 from the delivery configuration shown in FIG. 2 to the implanted configuration shown in FIG. 1 will now be described with reference to FIGS. 3 to 9. A guidewire 30 may be endoscopically introduced through the mouth and into the esophagus 104, the stomach 100, the pylorus 103, and the duodenum 102. As shown in FIG. 4 a proximal end 30a of the guidewire 30, located outside the patient, may be inserted through the axial passageway 25 of the sleeve delivery system 20, so that the sleeve delivery system can be advanced along the guidewire 30 towards a distal end 30b thereof, as shown in the progression in FIGS. 5 and 6. The sleeve delivery system 20 may be advanced along the guidewire 30 through an endoscope or may be introduced without an endoscope using a proximal marker arrangement. Alternatively, the sleeve delivery system 20 may be advanced along the guidewire 30 without an endoscope using fluoroscopy.

Figure 6:
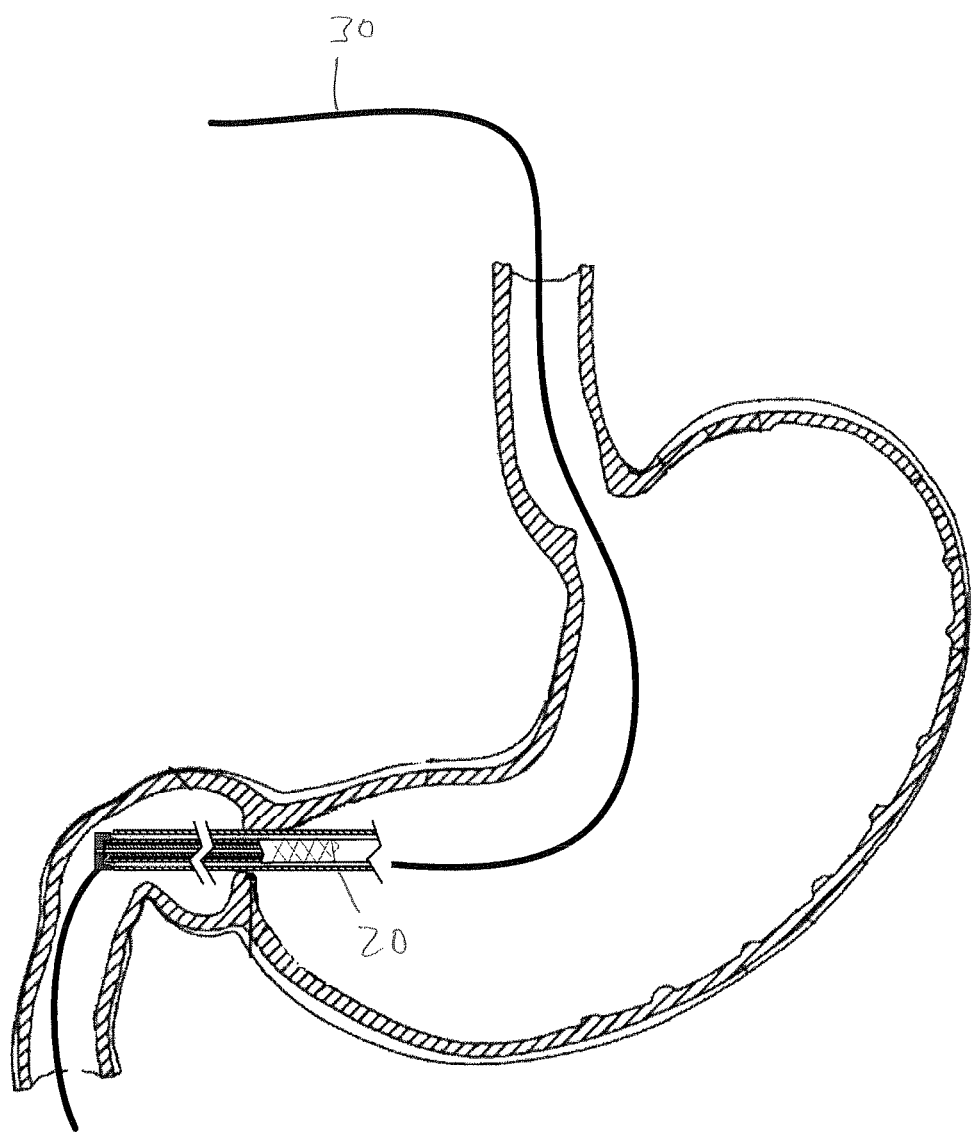
FIG. 6 shows the delivery system and the gastric implant advanced along the guidewire at the pyloric sphincter with a distal end of the gastric implant located in the duodenum and a proximal anchor portion of the gastric implant located in the stomach.
Figure 7:
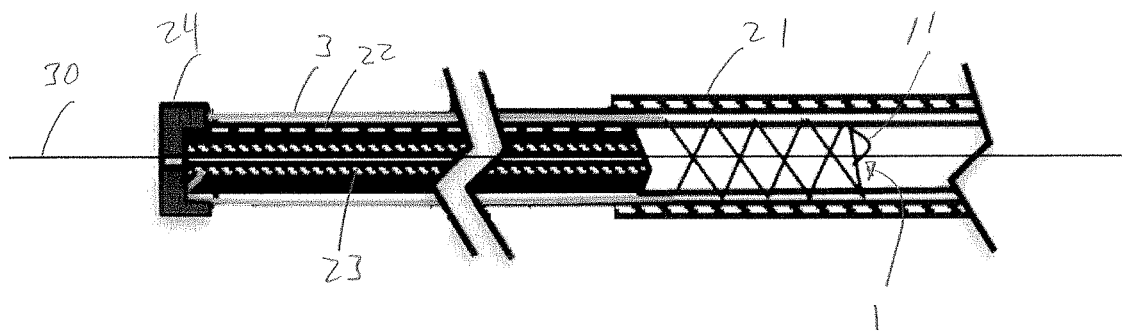
FIG. 7 shows a detailed view of the delivery system and gastric implant shown in FIG. 6 and with an outer sheath of the delivery system retracted.
Figure 8:
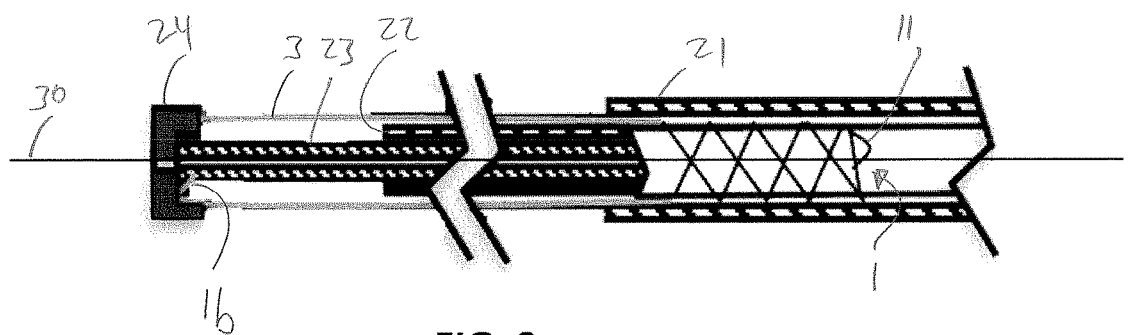
FIG. 8 shows a detailed view of the delivery system and gastric implant shown in FIG. 7 and with an intermediate sheath of the delivery system retracted.

When the sleeve delivery system is straddling the pylorus 103, as shown in FIG. 6, deployment of the implant 1 may commence. First, as shown in FIG. 7, the outer sheath is retracted to expose the distal sleeve portion 3 in the duodenum 102. The delivery system may be further positioned by advancing or retracting the entire sleeve delivery system 20 and implant device 1 while the outer sheath 21 is retracted to more precisely locate the pyloric restriction portion 4 in the pylorus 103, to locate the sealing portion within the duodenal bulb and pylorus 103, and to locate the proximal stomach anchor portion 2 in the stomach 100 adjacent to the pylorus 103. FIG. 8 shows that the intermediate sheath 22 is retracted relative to the inner sheath 23, which releases the distal end 1b of the distal sleeve portion 3 from the restraint between the intermediate sheath 22 and the inner sheath 23.

Figure 9:
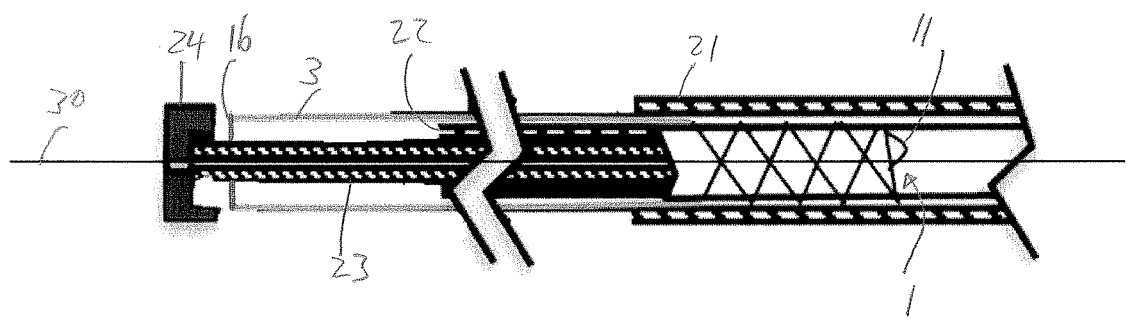
FIG. 9 shows a detailed view of the delivery system and gastric implant shown in FIG. 8 and with the cap and the distal end of the inner sheath extended proximally with respect to the distal end of the gastric implant to clear the end of the distal end of the gastric implant.
Figure 10:
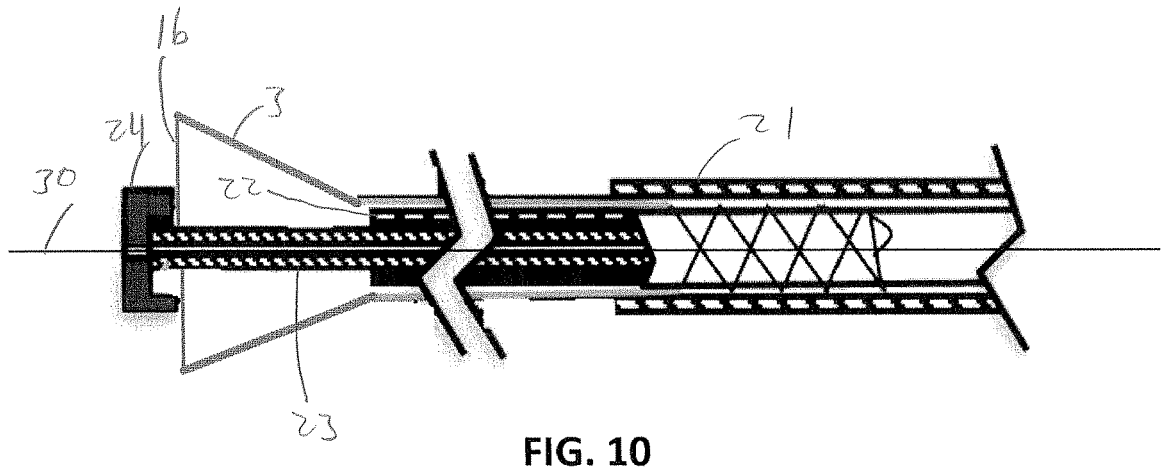
FIG. 10 shows a detailed view of the delivery system and gastric implant shown in FIG. 9 and with the distal end of the gastric implant radially expanded away from a cap of the delivery system.
Figure 11:
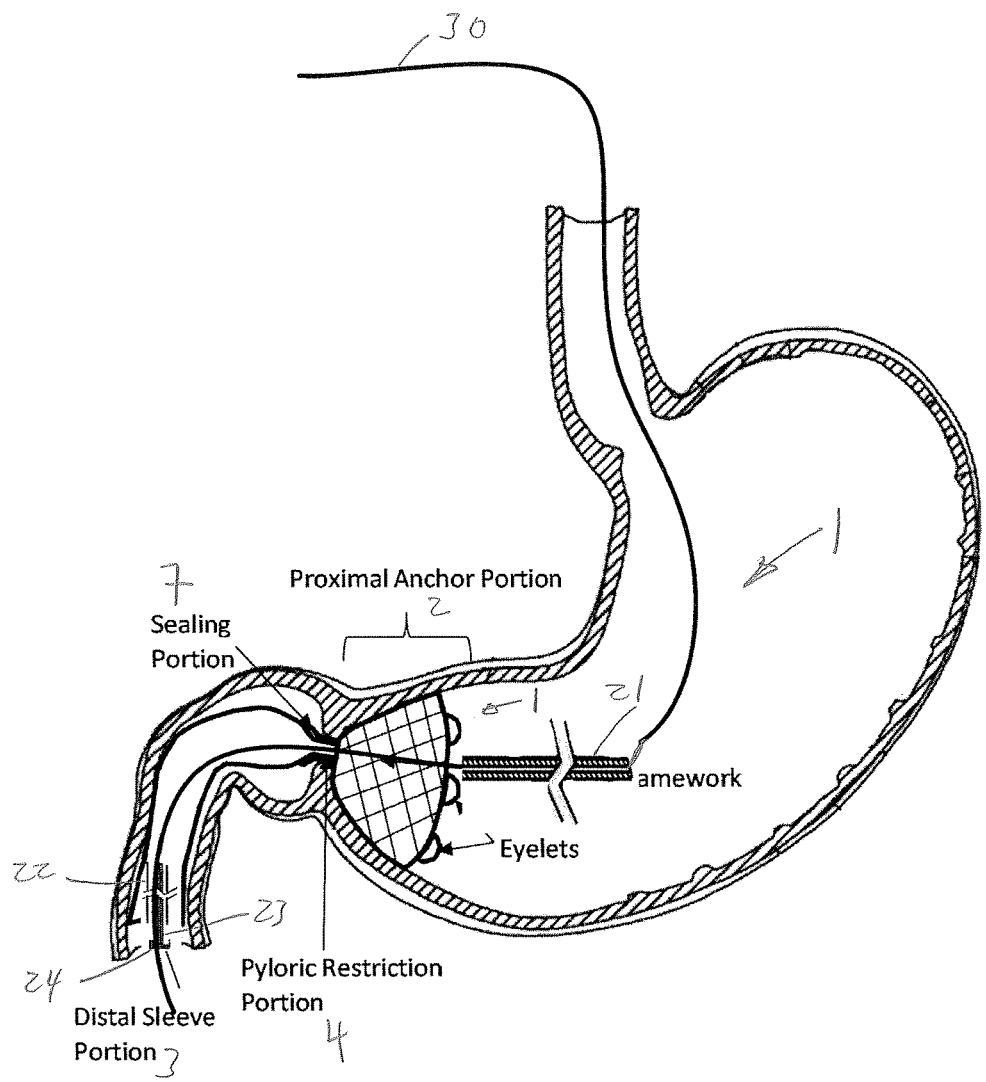
FIG. 11 shows the delivery system of FIG. 8 after the gastric implant has expanded and before the delivery system is withdrawn from the patient.
Figure 12:
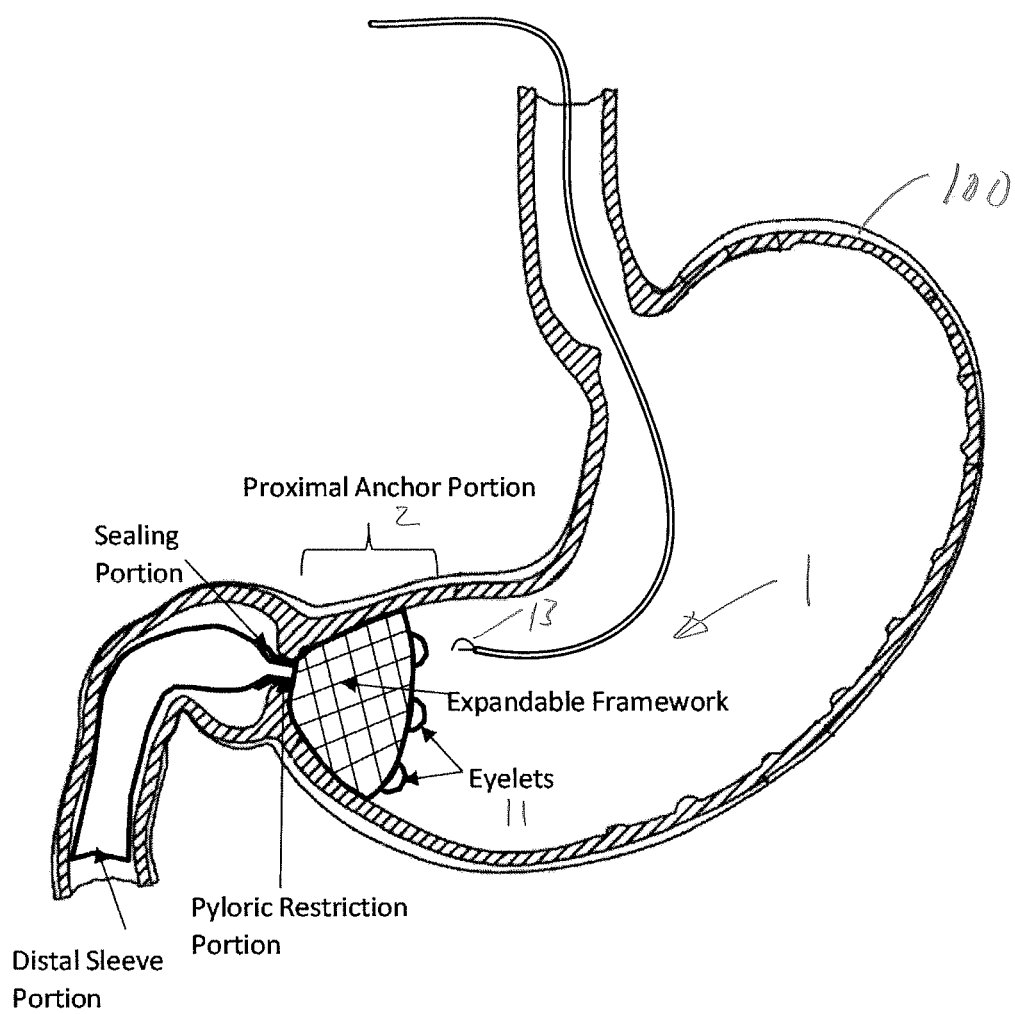
FIG. 12 shows the gastric implant in an expanded configuration with the delivery system of FIG. 11 removed and with an endoscopic suturing tool inserted into the stomach.
Figure 13:
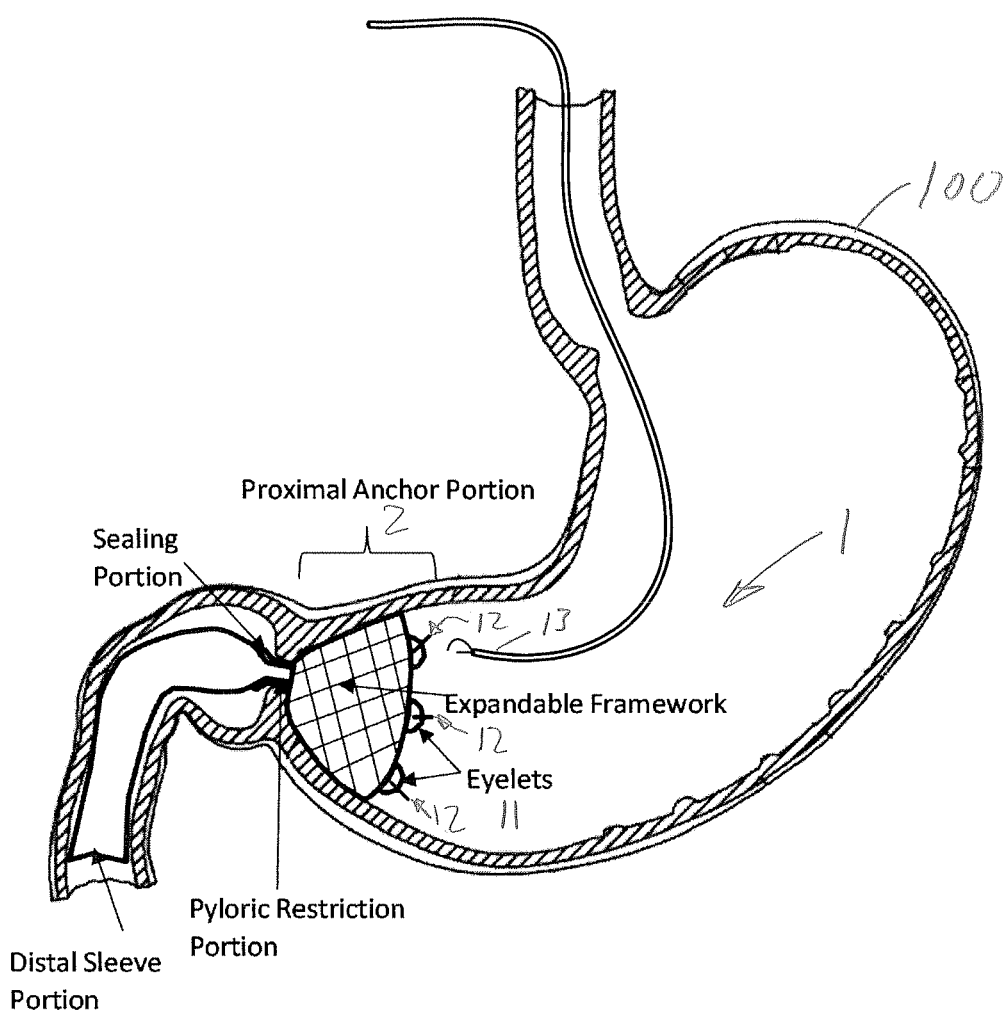
FIG. 13 shows the gastric implant with sutures fastening the eyelets of the proximal anchor portion to the stomach.

The inner sheath 23 is then distally displaced relative to the distal end 1b of the sleeve portion 3 to release the distal sleeve portion 3 from constraint, as shown in FIG. 9. When the distal end 1b of the distal sleeve portion 3 is released, it is free to expand radially outwardly away from the guidewire 30 to assume a diameter larger than the cap 24, as shown in FIG. 10. As the outer sheath 21 is retracted further, more of the distal sleeve portion 3 will be exposed and will expand. When the outer sheath 3 is fully retracted passed the proximal anchor portion 2, as shown in FIG. 11, the implant 1 will be disconnected from the sleeve delivery system 20 and the proximal anchor portion 2 will automatically expand inside the stomach 100 and eyelets 11 will be exposed. As shown in FIG. 11, the outer sheath 21 is proximal of the proximal anchor portion 2 and the cap 24, intermediate sheath 22, and the inner sheath 23 are inside the distal sleeve portion 3 in the duodenum after the distal sleeve portion 3 has expanded. The cap 24, intermediate sheath 22, and inner sheath 23 can be withdrawn proximally along the guidewire 30 through passageway 8 of the implant 1 and the outer sheath 21 can be withdrawn proximally along the guidewire 30. Once the delivery system 20 has been removed from the patient, the guidewire 30 may be withdrawn. Then, as shown in FIG. 12 an endoscopic suturing device 13 may be introduced into the stomach 100. The suturing device 13 is used to fasten (e.g., with sutures 12) the eyelets 11 of the proximal anchor portion 2 to the wall of the stomach 100, as shown in FIG. 13. The suturing device 13 may be withdrawn from the patient.

Figure 14:
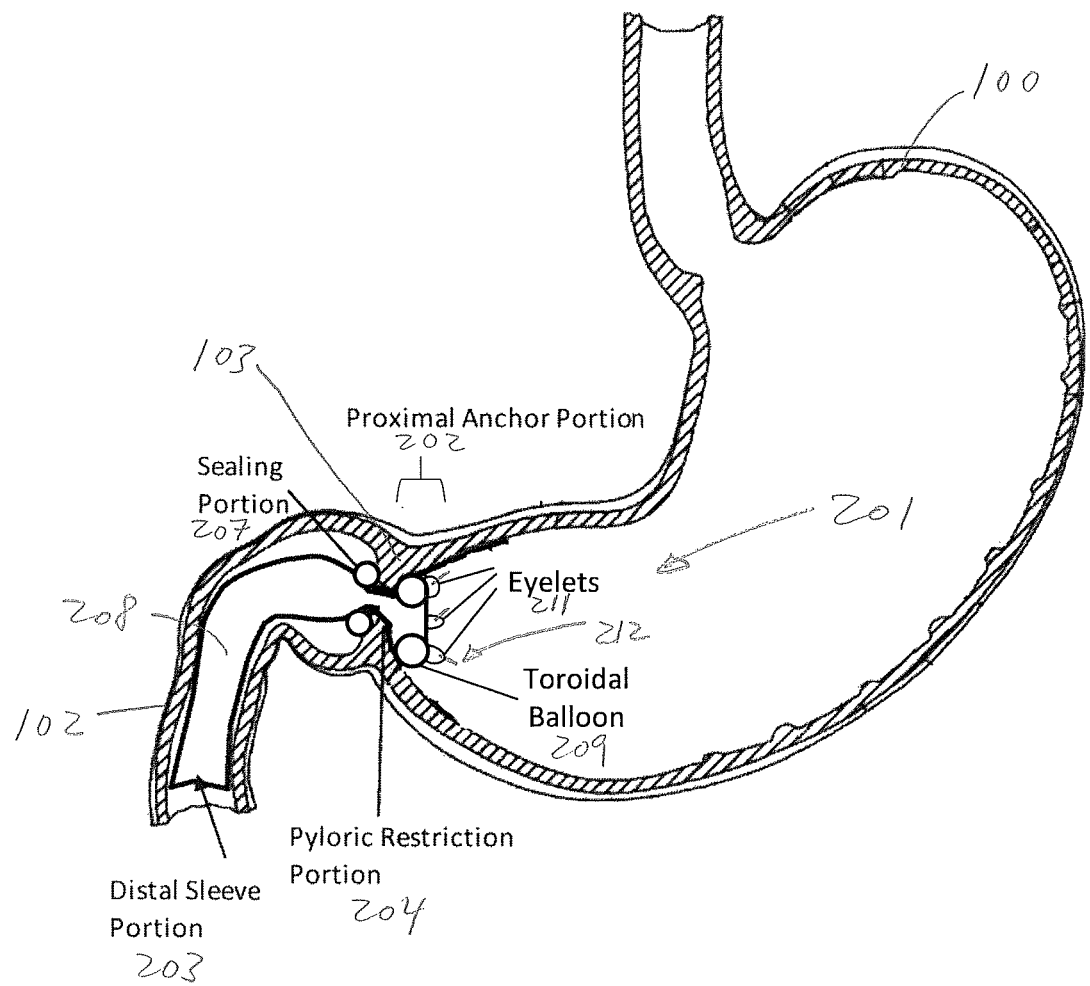
FIG. 14 shows another embodiment of a gastric implant device in an implanted configuration in a stomach of a patient.

FIG. 14 shows another embodiment of an implant 201, where elements corresponding to those of implant 1 are incremented by "200". The implant 201 in FIG. 14 includes a toroidal balloon 209, which substitutes for the expandable framework 9 of the implant 1. The balloon 209 may be introduced into the stomach in a deflated configuration (using a delivery catheter as described above with respect to implant 1) and inflated with a gas or a liquid after the balloon 209 is deployed and positioned proximally of the pylorus 103, as shown in FIG. 14. Preferably, the balloon 209 is configured to have an annular or toroidal shape such that the outer diameter of the balloon, when inflated, is larger than the diameter of the pylorus 103. In this manner, when the balloon 209 is inflated, the balloon 209 will be too large to move distally through the pylorus 103. Preferably, the outer surface of the balloon 209 will be compliant with the inner wall of the stomach 100 so that a seal may be formed therebetween when the balloon 209 is inflated. Also, the balloon 209 has eyelets 211, of similar construction to the eyelets 11 of implant 1 and are configured to be used in the same way to secure the balloon 209 to the stomach 100 using sutures 212. The balloon 209 defines a central opening through which stomach contents can flow into the pyloric restriction portion 204, which is attached to a distal side of the balloon 209. The balloon 209 may be self-sealing or may be provided with a port (not shown) for inflation and/or deflation, as is known in the art.

Also, in FIG. 14, the implant 201 has a sealing portion 207 in the form of a toroidal balloon. The toroidal balloon 207 may be introduced into the stomach in a deflated configuration (using a delivery catheter as described above with respect to implant 1) and inflated with a gas or a liquid after the balloon 207 is deployed and positioned distally of the pylorus 103, as show in FIG. 14. When the balloon 207 is inflated, it will help seal the annular space between the pyloric restriction portion 204 and the pylorus 103. The balloon 207 may be self-sealing or may be provided with a port (not shown) for inflation and/or deflation, as is known in the art.

While the balloons 209 and 207 are described above and shown in FIG. 14 as being toroidal, it will be appreciated that the balloons may be flatter and more generally be described as annular and may, in at least one embodiment, be formed as a conical shaped inflatable sleeve having an inflatable wall taking the place of the expandable framework 9 of the implant 1. These variations are not intended to be exhaustive, but are merely provided by way of example and not limitation. In addition, either of the balloons 207, 209 may be individually used in association the prior embodiments.

There have been described and illustrated herein several embodiments of a gastric implant and a method of implanting the gastric device. While particular embodiments of the invention have been described, it is not intended that the invention be limited thereto, as it is intended that the invention be as broad in scope as the art will allow and that the specification be read likewise. Thus, while particular materials and structures of the portions of the implant have been disclosed, it will be appreciated that other suitable materials and structures may be employed as well. It will therefore be appreciated by those skilled in the art that yet other modifications could be made to the provided invention without deviating from its spirit and scope as claimed.

What is claimed is:

1. A method of delivering and implanting a gastric implant in a gastrointestinal tract of a patient, the method comprising:
   providing the implant in a delivery catheter;
   delivering the gastric implant to a target location of the gastrointestinal tract wherein, delivering the implant includes delivering with a delivery system, the delivery system configured to receive and deliver the implant to a target location in the gastrointestinal tract of the patient, the delivery system including:
     an outer sheath,
     an intermediate sheath, radially spaced inward of the outer sheath
     an inner sheath disposed radially inward of the intermediate sheath, wherein the outer sheath, intermediate sheath, and the inner sheath are configured for relative axial displacement relative to one another, wherein the implant is disposed in the elongate delivery configuration between the outer sheath and the intermediate sheath and a distal end of the implant is disposed between the intermediate sheath and the inner sheath;
   deploying the implant with the delivery catheter at the target location; and
   fastening an anchor portion of the implant to a lower stomach of the gastrointestinal tract.

2. The method according to claim 1, wherein:
   deploying the implant includes retracting the outer sheath relative to the intermediate and inner sheaths to expose an outer surface of the implant.

3. The assembly according to claim 2, wherein:
   deploying the implant includes outwardly expanding the implant.

4. The method according to claim 1, wherein:
   the delivery system includes a cap connected to a distal end of the inner sheath and a distal end of the implant is disposed in the cap, and
   deploying the implant includes retracting the outer sheath relative to the intermediate and inner sheaths to expose an outer surface of the implant, and then distally displacing the inner sheath and cap relative to the intermediate sheath to release the distal end of the gastric implant from the cap.

5. The method according to claim 4, wherein:
   deploying the implant further includes withdrawing the cap through the gastric implant.

6. The method according to claim 1, wherein:
   the target location includes at least one of the stomach, duodenum, and the pylorus.

7. The method according to claim 6, wherein:
   the implant is delivered endoscopically.

8. The method according to claim 7, wherein:
   the implant is fastened with at least one suture.

9. The method according to claim 8, wherein:
   the implant has at least one eyelet that is sutured to the stomach.

* * * * *